United States Patent
Muni et al.

(12)

(10) Patent No.: US 6,454,741 B1
(45) Date of Patent: Sep. 24, 2002

(54) ASPIRATION METHOD

(75) Inventors: Ketan P. Muni, San Jose; Gholam Reza Zadno-Azizi, Newark; Celso Bagaoisan, Union City, all of CA (US)

(73) Assignee: Medtronic Percusurge, Inc., Santa Rosa, CA (US)

( * ) Notice: Subject to any disclaimer, the term of this patent is extended or adjusted under 35 U.S.C. 154(b) by 0 days.

(21) Appl. No.: 09/537,471

(22) Filed: Mar. 24, 2000

Related U.S. Application Data

(63) Continuation of application No. 09/049,857, filed on Mar. 27, 1998, now Pat. No. 6,135,991, which is a continuation-in-part of application No. 08/813,807, filed on Mar. 6, 1997, now abandoned.

(51) Int. Cl.$^7$ .......................... A61M 29/00; A61M 31/00
(52) U.S. Cl. ..................................... 604/96.01; 604/509
(58) Field of Search ................................ 604/915–921, 604/507–509, 96.01, 109, 164.13; 606/192–200; 600/585, 434

(56) References Cited

U.S. PATENT DOCUMENTS

| | | |
|---|---|---|
| 3,144,868 A | 8/1964 | Jascalevich |
| 4,276,874 A | 7/1981 | Wolvek et al. |
| 4,445,892 A | 5/1984 | Hussein et al. |
| 4,456,011 A | 6/1984 | Warnecke |
| 4,468,216 A | 8/1984 | Muto |
| 4,511,354 A | 4/1985 | Sterling |
| 4,573,966 A | 3/1986 | Weikl et al. |
| 4,610,662 A | 9/1986 | Weikl et al. |
| 4,636,195 A | 1/1987 | Wolinsky |
| 4,655,746 A | 4/1987 | Daniels et al. |
| 4,692,139 A | 9/1987 | Stiles |
| 4,696,668 A | 9/1987 | Wilcox |
| 4,705,507 A | 11/1987 | Boyles |
| 4,714,460 A | 12/1987 | Calderon |
| 4,748,982 A | 6/1988 | Horzewski et al. |
| 4,781,677 A | 11/1988 | Wilcox |
| 4,790,812 A | 12/1988 | Hawkins, Jr. et al. |
| 4,790,813 A | 12/1988 | Kensey |
| 4,824,436 A | 4/1989 | Wolinsky |
| 4,832,028 A | 5/1989 | Patel |
| 4,838,268 A | 6/1989 | Keith et al. |
| 4,911,163 A | 3/1990 | Fina |

(List continued on next page.)

FOREIGN PATENT DOCUMENTS

| | | |
|---|---|---|
| DE | 38 04 849 A1 | 2/1987 |
| WO | WO/89/01309 | 2/1989 |
| WO | WO/95/09024 | 4/1995 |

(List continued on next page.)

OTHER PUBLICATIONS

"Angioplasty and Interventional Vascular Procedures in thePeripheral, Renal, Visceral and Extracranial Circulation", Wholey, et al., II–Coronary and Peripheral Angioplasty, Chapter 33, pp. 600–628.

(List continued on next page.)

Primary Examiner—Michael J. Hayes
Assistant Examiner—Michelle Lewis
(74) Attorney, Agent, or Firm—Knobbe, Martens, Olson and Bear, LLP.

(57) ABSTRACT

A method for the treatment of a stenosis or an occlusion in a blood vessel in which an occlusive device is first delivered and activated at a site distal to the occlusion to at least partially occlude the vessel. A therapy catheter is then introduced to treat the occlusion and a debris removal device is delivered to aspirate debris from the vessel. The present invention eliminates the need for a separate irrigation catheter and irrigation fluid which allows the procedure to be performed quickly and efficiently, and is especially useful in the removal of occlusion from saphenous vein graft, the coronary and carotid arteries, arteries above the aortic arch and vessels of similar size and pressure.

68 Claims, 9 Drawing Sheets

U.S. PATENT DOCUMENTS

| | | |
|---|---|---|
| 4,921,478 A | 5/1990 | Solano et al. |
| 4,926,858 A | 5/1990 | Gifford, III et al. |
| 4,946,466 A | 8/1990 | Pinchuk et al. |
| 4,950,238 A | 8/1990 | Sullivan |
| 4,964,409 A | 10/1990 | Tremulis |
| 5,000,743 A | 3/1991 | Patel |
| 5,035,686 A | 7/1991 | Crittenden et al. |
| 5,059,178 A | 10/1991 | Ya |
| 5,135,484 A | 8/1992 | Wright |
| 5,152,277 A | 10/1992 | Honda et al. |
| 5,163,905 A | 11/1992 | Don Michael |
| 5,163,906 A | 11/1992 | Ahmadi |
| 5,167,239 A | 12/1992 | Cohen et al. |
| 5,195,955 A | 3/1993 | Don Michael |
| 5,221,270 A | 6/1993 | Parker |
| 5,226,889 A | 7/1993 | Sheiban |
| 5,250,060 A | 10/1993 | Carbo et al. |
| 5,256,141 A | 10/1993 | Gencheff et al. |
| 5,279,546 A | 1/1994 | Mische et al. |
| 5,281,200 A | 1/1994 | Corso, Jr. et al. |
| 5,320,604 A | 6/1994 | Walker et al. |
| 5,320,605 A | 6/1994 | Sahota |
| 5,322,508 A | 6/1994 | Viera |
| 5,328,471 A | 7/1994 | Slepian |
| 5,342,306 A | 8/1994 | Don Michael |
| 5,380,284 A | 1/1995 | Don Michael |
| 5,395,311 A | 3/1995 | Andrews |
| 5,397,307 A | 3/1995 | Goodin |
| 5,403,274 A | 4/1995 | Cannon |
| 5,405,322 A | 4/1995 | Lennox et al. |
| 5,413,558 A | 5/1995 | Paradis |
| 5,415,635 A | 5/1995 | Bagaoisan et al. |
| 5,415,636 A | 5/1995 | Forman |
| 5,423,742 A | 6/1995 | Theron |
| 5,423,744 A | 6/1995 | Gentcheff et al. |
| 5,439,000 A | 8/1995 | Gunderson et al. |
| 5,439,446 A | 8/1995 | Barry |
| 5,449,343 A | 9/1995 | Samson et al. |
| 5,458,573 A | 10/1995 | Summers |
| 5,458,574 A | 10/1995 | Machold et al. |
| 5,460,610 A | 10/1995 | Don Michael |
| 5,462,529 A | 10/1995 | Simpson et al. |
| 5,464,394 A | 11/1995 | Millet et al. |
| 5,476,450 A | 12/1995 | Ruggio |
| 5,478,309 A | 12/1995 | Sweezer et al. |
| 5,484,412 A | 1/1996 | Pierpont |
| 5,496,346 A | 3/1996 | Horzewski et al. |
| 5,500,180 A | 3/1996 | Anderson et al. |
| 5,505,700 A | 4/1996 | Leone et al. |
| 5,505,702 A | 4/1996 | Arney |
| 5,514,092 A | 5/1996 | Forman et al. |
| 5,599,307 A | 2/1997 | Bacher et al. |
| 5,634,897 A | 6/1997 | Dance et al. |
| 5,645,533 A | 7/1997 | Blesser et al. |
| 5,674,198 A | 10/1997 | Leone |
| 5,681,336 A | 10/1997 | Clement et al. |
| 5,688,234 A | 11/1997 | Frisbie |
| 5,779,721 A | 7/1998 | Nash |
| 5,823,996 A | 10/1998 | Sparks |
| 5,827,229 A | 10/1998 | Auth et al. |
| 5,833,644 A | 11/1998 | Zadno-Azizi et al. |
| 5,833,650 A | 11/1998 | Imran |
| 5,879,361 A | 3/1999 | Nash |
| 5,941,896 A | 8/1999 | Kerr |
| 5,954,745 A | 9/1999 | Gertler et al. |
| 6,022,336 A | 2/2000 | Zadno-Azizi et al. |
| 6,135,991 A | 10/2000 | Muni et al. |
| 6,152,909 A | 11/2000 | Bagaoisan et al. |
| 6,309,399 B1 * | 10/2001 | Barbut et al. ............... 606/159 |

FOREIGN PATENT DOCUMENTS

| | | |
|---|---|---|
| WO | WO/96/01079 | 1/1996 |
| WO | WO 96/15824 | 5/1996 |
| WO | WO/97/44082 | 11/1997 |
| WO | WO/98/26833 | 6/1998 |
| WO | WO/98/38930 | 9/1998 |
| WO | WO/98/44982 | 10/1998 |
| WO | WO/99/22673 | 5/1999 |

OTHER PUBLICATIONS

"DCA Device" (section) and summary III–Coronary Atherectomy, Chapter 35, pp. 642, 657, and 658.

"Zeppelin: Balloon Guiding Catheter", Micro Interventional Systems, Inc. Advertisement.

"Coronary and Peripheral Angioplasty: Historic Perspective" Myler, et al., II–Coronary and Peripheral Angioplasty, Chapter 9, pp. 171–185.

"Restenosis: The Clinical Issues" Hillegass, et al., II–Coronary and Peripheral Angioplasty, Chapter 22, pp. 415–435.

"The Pathology of Interventional Coronary Artery Techniques and Devices" Waller, et al., II–Coronary and Peripheral Angioplasty, Chapter 24, pp. 449–476.

"Perfusion Angioplasty:"Kereiakes, et al., II–Coronary and Peripheral Angioplasty, Chapter 25, pp. 477–494.

"Percutaneous Coronary Rotational Angioplasty with the Rotablator" Bertrand, et al., III–Coronary Atherectomy, Chapter 36, pp. 659, 666 and 667.

"Extraction Atherectomy" III–Coronary Atherectomy, Chapter 37, pp. 669, 675–677.

"Zeppelin–1066: Flow Control and Protection During Carotid Angioplasty" Micro Interventional Systems, Inc., Advertisement.

"Zeppelin–1066: Flow Control Improves Safety During CCF Embolization" Mirco Interventional Systems, Inc., Advertisement.

"Zeppelin–1066: Provides Flow Control and Protection During Detachable Ballon Occlusion" Micro Interventional Systems, Inc., Advertisement.

"Carotid Endarterectomy" Hershey/Calman, Atlas of Vascular Surgery, pp. 311–318, 1973.

"Percutaneous Transluminal Angioplasty in Arteriosclerotic Internal Carotid Artery Stenosis" Bockenheimer, et al., AJNR, 4:791–792, May/Jun. 1983.

"Percutaneous Transluminal Angioplasty of the Carotid Artery" Tsai, et al., AJNR, 7:349–358, Mar./Apr. 1986.

"Practical Aspects of Percutaneous Transluminal Angioplasty of the Carotid Artery" Tsai, et al., ACTA Radiological, Supplementum 369, XIII Symposium Neuroradiologicum Stockholm, Jun. 1986.

"Transluminal Angioplasty for the Treatment of Carotid Artery Stenosis" Freitag, et al., VASA, Band 16, Heft 1, 1987.

"Feasibility of Percutaneous Transluminal Angioplasty for Carotid Artery Stenosis" Brown, et al., Journal of Neurology, Neurosurgery, and Psychiatry, 53(3): 238–243, Mar. 1990.

"Percutaneous Angioplasty of Artherosclerotic Carotid Arteries" Porta, et al., Cerebrovasc Dis., 1:265–272, 1991.

"Percutaneous Transluminal Angioplasty (PTA) of Supra–Aortic Arteries Especially the Internal Carotid Artery" Kachel, et al., Neuroradiology, 33(3): 191–194, 1991.

"Carotid Angioplasty: Haemodynamic and Embolic Consequences" Markus, et al., Cerebrovascular Diseases, Abstract 214, p. 259, Jul.–Aug. 1994.

"Carotid Endarterectomy: The Gold Standard" Zarins, Journal of Endovasculary Surgery, 3(1): pp. 10–15, Feb. 1996.

"Angiojet® System Used to Treat Stroke Victim" Possis Medical, Inc., News Release, Sep. 11, 1996.

"Current and Future Treatment of Carotid Bifurcation Atherosclerotic Disease: A Perspective" Becker, Journal of Vascular and Interventional Radiology, 8(1); 3–8, Jan.–Feb. 1997.

"Percutaneous Angioplasty of Atherosclerotic and Postsurgical Stenosis of Carotid Arteries" J. Theron et al., AJNR, 6:495–500, May/Jun. 1987.

* cited by examiner

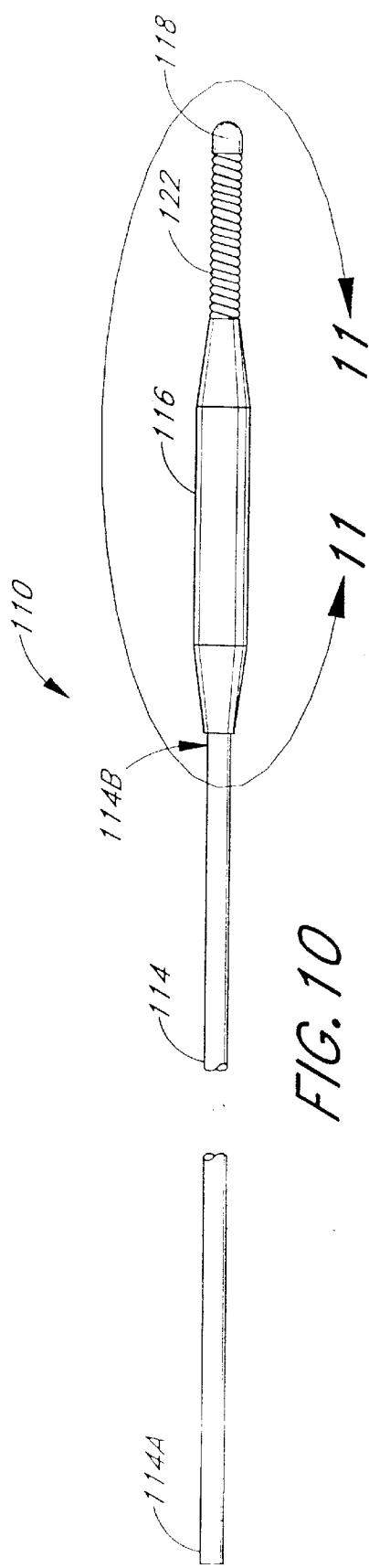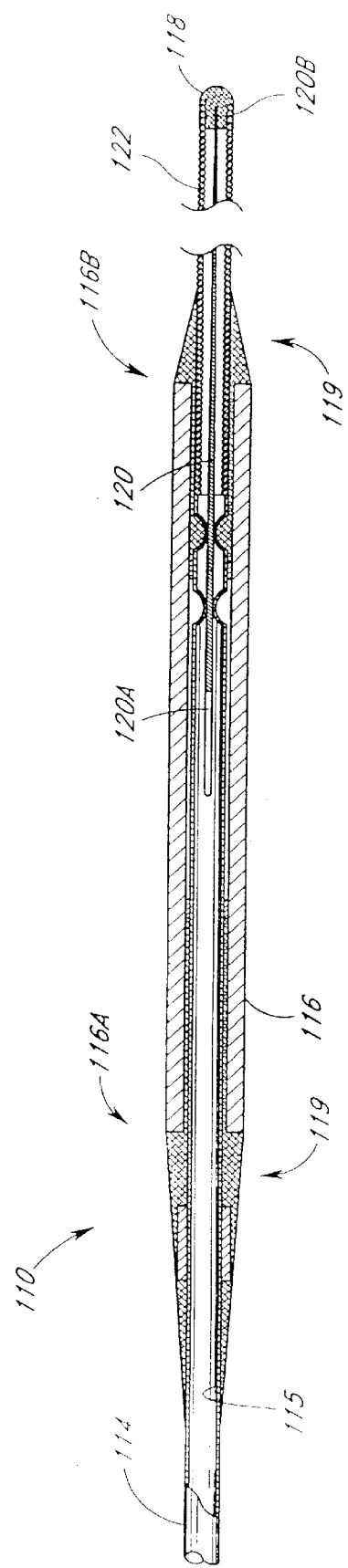
FIG. 10
FIG. 11

ASPIRATION METHOD

CROSS-REFERENCE TO RELATED APPLICATIONS

This application is a continuation of U.S. patent application Ser. No. 09/049,857, filed Mar. 27, 1998, now U.S. Pat. No. 6,135,991, which is a continuation-in-part of U.S. patent application Ser. No. 08/813,807, filed Mar. 6, 1997, now abandoned, which is hereby incorporated by reference in its entirety.

BACKGROUND OF THE INVENTION

1. Field of the Invention

The present invention relates to an improved method for aspirating emboli, thrombi, and other types of particles from the human arterial or venous system, the method being particularly well suited for treating stenoses or occlusions within saphenous vein grafts, coronary arteries, arteries above the aortic arch such as the carotid and cerebral arteries, and similar vessels.

2. Description of the Related Art

Human blood vessels often become occluded or completely blocked by plaque, thrombi, other deposits, emboli or other substances, which reduce the blood carrying capacity of the vessel. Should the blockage occur at a critical place in the circulatory system, serious and permanent injury, or even death, can occur. To prevent this, some form of medical intervention is usually performed when significant occlusion is detected.

Coronary heart disease is an extremely common disorder in developed countries, and is the leading cause of death in the U.S. Damage to or malfunction of the heart is caused by narrowing or blockage of the coronary arteries (atherosclerosis) that supply blood to the heart. The coronary arteries are first narrowed and may eventually be completely blocked by plaque, and may further be complicated by the formation of thrombi (blood clots) on the roughened surfaces of the plaques. Myocardial infarction can result from atherosclerosis, especially from an occlusive or near occlusive thrombi overlying or adjacent to the atherosclerotic plaque, leading to death of portions of the heart muscle. Thrombi and emboli also often result from myocardial infarction, and these clots can block the coronary arteries, or can migrate further downstream, causing additional complications.

Various types of intervention techniques have been developed which facilitate the reduction or removal of the blockage in the blood vessel, allowing increased blood flow through the vessel. One technique for treating stenosis or occlusion of a blood vessel is balloon angioplasty. A balloon catheter is inserted into the narrowed or blocked area, and the balloon is inflated to expand the constricted area. In many cases, near normal blood flow is restored. It can be difficult, however, to treat plaque deposits and thrombi in the coronary arteries, because the coronary arteries are small, which makes accessing them with commonly used catheters difficult.

Other types of intervention include atherectomy, deployment of stents, introduction of specific medication by infusion, and bypass surgery. Each of these methods are not without the risk of embolism caused by the dislodgement of the blocking material which then moves downstream. In addition, the size of the blocked vessel may limit percutaneous access to the vessel.

In coronary bypass surgery, a more costly and invasive form of intervention, a section of a vein, usually the saphenous vein taken from the leg, is used to form a connection between the aorta and the coronary artery distal to the obstruction. Over time, however, the saphenous vein graft may itself become diseased, stenosed, or occluded, similar to the bypassed vessel. Atherosclerotic plaque in saphenous vein grafts tends to be more friable and less fibrocalcific than its counterpart in native coronary arteries.

Diffusely diseased old saphenous vein grafts with friable atherosclerotic lesions and thrombi have therefore been associated with iatrogenic distal embolic debris. Balloon dilatation of saphenous vein grafts is more likely to produce symptomatic embolization than dilatation of the coronary arteries, not only because of the difference in the plaque but also because vein grafts and their atheromatous plaques are generally larger than the coronary arteries to which they are anastomosed. Once the plaque and thrombi are dislodged from the vein, they can move downstream, completely blocking another portion of the coronary artery and causing myocardial infarction. In fact, coronary embolization as a complication of balloon angioplasty of saphenous vein grafts is higher than that in balloon angioplasty of native coronary arteries. Therefore, balloon angioplasty of vein grafts is performed with the realization that involvement by friable atherosclerosis is likely and that atheroembolization represents a significant risk.

Because of these complications and high recurrence rates, old diffusely diseased saphenous vein grafts have been considered contraindications for angioplasty and atherectomy, severely limiting the options for minimally invasive treatment. However, some diffusely diseased or occluded saphenous vein grafts may be associated with acute ischemic syndromes, necessitating some form of intervention.

There is therefore a need for improved methods of treatment for occluded vessels such as saphenous vein grafts and the smaller coronary arteries, the carotid and cerebral arteries, which decrease the risks to the patient.

SUMMARY OF THE INVENTION

The present invention provides a novel method for removing plaque, thrombi, emboli and other types of obstructions or occlusions from blood vessels having an inlet fluid pressure of at least 0.2 psi at any time during the diastolic/systolic cycle of the heart. Although the pressure within the vessel may fall below 0.2 psi during relaxation between heartbeats, so long as the pressure created by the heartbeat rises to at least 0.2 psi, the pressure within the vessel will be sufficient. The method preferably includes the use of an occlusive device such as a balloon or filter to occlude the vessel distal to the obstruction, an optional therapy catheter to treat the obstruction, and a source of aspiration to remove the debris created by the therapy. By utilizing the fluid pressure and flow within the blood vessel, this method eliminates the need for a separate irrigation catheter and irrigation fluid. The present invention allows for the removal of occlusions more rapidly than known methods. Speed is essential in such procedures, since blood flow is significantly decreased or stopped during the time the vessel is occluded. The speed with which normal blood flow is restored is more critical in main vessels which supply blood to collateral vessels. The method of the present invention allows for the removal of occlusions from saphenous vein grafts, coronary arteries, arteries above the aortic arch such as the carotid and cerebral arteries, and blood vessels of similar pressure. The minimally invasive treatment can be provided at low cost and at relatively low risk to the patient.

In accordance with one aspect of the present invention, there is provided a method for the treatment of a stenosis or an occlusion in a blood vessel having a fluid pressure of at least about 0.2 psi. The blood vessel can be a saphenous vein graft, a coronary artery, a blood vessel above the aortic arch, or any other vessel with a fluid flow rate of at least about 10 cc per minute (prior to occlusion of the vessel using an occlusive device as described below), and more preferably, about 60 to 80 cc per minute, or about 120 to 140 cc per minute. This flow rate is needed to provide adequate irrigation fluid, which allows for substantially complete aspiration of the area surrounding the occlusion in a very short period of time. Using this combination of irrigation provided from the blood flow into the vessel and aspiration, it has been found that aspiration of debris and fluid within the working area can occur in less than 3 seconds, but can also continue for 10 to 20 seconds or longer, until the procedure is completed. Thus, the physician can quickly and efficiently clear the debris from the area and restore normal blood flow through the vessel.

One aspect of the method comprises first inserting a catheter or guidewire having an occlusive device at its distal end into the blood vessel, until it is distal to the stenosis or occlusion. It is to be understood that the stenosis or occlusion could be in a discrete location or diffused within the vessel. Therefore, although placement of the occlusive device is said to be distal to the stenosis or occlusion to be treated, portions of the diffuse stenosis or occlusion may remain distal to the occlusive device.

Once in place, the occlusive device is activated to substantially or completely occlude the vessel distal to the existing stenosis or occlusion and to create a working area surrounding the stenosis or occlusion. A therapy catheter is then inserted into the blood vessel until it reaches the stenosis or occlusion, and a desired therapy is performed on the stenosis or occlusion. The fluid inlet pressure within the vessel prevents any particles produced during therapy from flowing against the pressure and out of the working area, thus localizing the particles for aspiration. The therapy catheter is removed, and the distal end of an aspiration catheter or other device which creates an area of turbulence and uses negative pressure to aspirate fluid and debris is delivered into the vessel with the preferred placement being at the working area in a position just proximal to the occlusive device. Fluid is aspirated from the working area inside the vessel preferably proximal to the occlusive device to remove debris, while the fluid pressure within the vessel provides irrigation fluid within the working area. This aspiration creates a fluid flow within the working area, and provides a flow of irrigation fluid into the area. It is this combination of irrigation and aspiration that allows for very fast and efficient removal of debris. Once aspiration is complete, the aspiration catheter or similar device is removed and the occlusive device deactivated. Finally, the catheter or guidewire is removed from the vessel as well.

The insertion can include the act of inserting the proximal end of the guidewire into the hollow lumen inside the aspiration catheter and advancing the aspiration catheter over the guidewire. This is commonly known as "over-the-wire" insertion. Alternatively, the proximal end of the guidewire can be inserted into a separate guidewire lumen on the aspiration catheter. Only a short portion of the aspiration catheter, as little as 5 cm, rides over the guidewire as the catheter is advanced. This is known as a single operator system, since, unlike the over-the-wire systems, a second operator is not required to hold the long guidewire while the catheter is inserted into the patient; a single user alone can deliver the catheter over the guidewire in this system.

The distal end of the aspiration catheter or similar device should be slidably inserted into the vessel, across the occlusion and preferably as close to the proximal side of the occlusive device as possible. Thereafter, aspiration is begun and the aspiration catheter should be pulled back by the operator, such that the distal tip slides proximal to the occlusion and the occlusive device. Thus, while the distal tip of the aspiration catheter is preferably initially at a position distal to the occlusion and no more than about 5 cm proximal to the occlusive device, or preferably no more than about 2 cm proximal to the occlusive device, the operator then slides the aspiration catheter back during aspiration, crossing the occlusion and increasing the distance between the distal tip and the occlusive device. Aspiration can therefore occur anywhere between about 0 to 20 cm proximal to the occlusive device. Alternatively, the distal tip of the aspiration catheter may be initially positioned proximal to the occlusion and the occlusive device. Aspiration is begun, and the tip is moved in a distal direction, across the occlusion and immediately adjacent the occlusive device. The tip is then moved in a proximal direction, back across the occlusion. This distal and proximal movement of the catheter tip during aspiration ensures the complete removal of particles and debris from the patient.

The irrigation fluid supplied by the proximal portion of the blood vessel will move any particles or debris from a position proximal to the distal end of the aspiration catheter, thus allowing them to be aspirated. If a particle, however, is too far distal to the tip of the aspiration catheter, the irrigation fluid will tend to keep it there and not allow it to be aspirated from the vessel. The tip of the aspiration catheter can therefore be slidably advanced in a distal direction more than once if desired, to ensure complete removal of debris. Once aspiration has begun, additional blood will flow into the area, creating turbulence and also allowing for the removal of debris.

If desired, a guide catheter can first be inserted into the patient's body to aid in the insertion of the guidewire and catheters. The guide catheter can be used to provide aspiration in place of the aspiration catheter if desired. The guide catheter is then removed following completion of the procedure.

In accordance with another aspect of the present invention, there is provided a method for the treatment of a stenosis or an occlusion in a blood vessel having a fluid pressure of at least about 0.2 psi, and a fluid flow rate of at least about 10 cc per minute (when not occluded using an occlusive device as described), and more preferably, about 60 to 80 cc per minute, or 120–140 cc per minute. The method comprises the steps of inserting a guidewire or catheter having an occlusive device on its distal end into the blood vessel, until the occlusive device is distal to the stenosis or occlusion. The occlusive device is activated to substantially occlude the vessel distal to the existing stenosis or occlusion and create a working area surrounding the stenosis or occlusion. A therapy catheter is then inserted into the lumen of an aspiration catheter or similar device, and the therapy catheter and the aspiration catheter are simultaneously delivered into the blood vessel until they reach the stenosis or occlusion. Therapy is performed to eliminate the occlusion, and the fluid pressure within the vessel acts to prevent any particles produced during therapy from flowing against the pressure and out of the working area. When therapy is complete, the therapy catheter is removed while the aspiration catheter remains, and fluid inside the working area is aspirated to remove the particles while the fluid pressure provides irrigation fluid within the working area.

When aspiration is complete, the aspiration catheter or similar device is removed and the occlusive device is deactivated. The guidewire or catheter is also then removed.

In accordance with yet another aspect of the present invention, there is provided a method for the treatment of a stenosis or an occlusion in a blood vessel having a fluid pressure of at least about 0.2 psi, and a fluid flow rate of at least about 10 cc per minute (prior to occlusion using an occlusive device). The method comprises inserting an occlusive device into the vessel until the occlusive device is distal to the stenosis or occlusion. The device can be attached to the distal end of a catheter or guidewire. The device is actuated to occlude the vessels distal to the existing stenosis or occlusion and create a working area surrounding the stenosis or occlusion. The fluid pressure within the vessel prevents any particles dislodged during insertion of the guidewire or catheter from flowing against the pressure and out of the working area. The distal end of an aspiration catheter or similar device is inserted to a position just proximal to the occlusive device, and fluid from the working area inside the vessel just proximal the occlusive device is aspirated. This will remove the stenosis or occlusion and any free particles while the fluid pressure provides irrigation fluid within the area. When aspiration is complete, the aspiration catheter is removed and the occlusive device deactivated. The guidewire or catheter is then removed.

Another aspect of the present invention involves the use of an expandable device, such as an inflatable balloon, to inhibit the migration of emboli or other particles in a proximal to distal direction within the vessel. This can be done by at least partially occluding the vessel at a site distal to the emboli or other occlusion. Again, although placement of the expandable device is said to be distal to the emboli or other occlusion to be treated, in the case of a diffuse occlusion, outlying portions of the occlusion may remain distal to the device.

The fluid pressure within the vessel prevents emboli or other particles from migrating in a distal to proximal direction. If desired, a therapy catheter may be used to perform therapy on the vessel at the site of the emboli or occlusion. The therapy catheter may be removed, and a catheter, such as an aspiration catheter, having a lumen in fluid communication with a distal opening in the catheter is advanced across the site of the emboli or occlusion such that the opening is distal to at least a portion of the emboli or occlusion. Fluid is then drawn through the distal opening in the catheter to remove the emboli, occlusion or debris. By drawing fluid into the opening, a fluid flow is created in the lumen of the catheter in a distal to proximal direction, while simultaneously, fluid flows in a proximal to distal direction in the vessel.

In accordance with yet another aspect of the invention, there is provided a method for the evacuation of emboli from a blood vessel. A catheter having a lumen in fluid communication with a distal opening in the catheter is positioned such that the opening is distal to at least a portion of an occlusive substance, such as emboli, within the blood vessel. Fluid is then drawn from the vessel into the distal opening such that the emboli are carried from the vessel into the distal opening and through the lumen of the catheter. The fluid intake preferably simultaneously creates a fluid flow in the lumen in a distal to proximal direction, and in the vessel in a proximal to distal direction. During the fluid intake through the catheter, the distal opening in the catheter is preferably moved from a position distal to the occlusive substance, to a position proximal to the occlusive substance, to a position distal to the occlusive substance to ensure complete removal of particles.

Accordingly, the present invention provides for very fast and efficient aspiration of an area surrounding an occlusion in a blood vessel. The patient's own blood provides the irrigation fluid, thereby eliminating the need for a separate irrigation catheter and supply of irrigation fluid. By reducing the number of devices needed to be inserted into the patient, the present invention reduces the amount of time required to complete the procedure, and allows the physician to restore normal blood flow in the vessel in a very short period of time.

BRIEF DESCRIPTION OF THE DRAWINGS

FIG. 10 is a schematic view of a catheter apparatus for use in the method of the present invention;

FIG. 11 is a schematic cross-sectional view of a distal portion of the catheter apparatus shown in FIG. 10.

DETAILED DESCRIPTION OF THE PREFERRED EMBODIMENT

The present invention provides an improved method for aspirating emboli, plaque, thrombi or other occlusions from a blood vessel. A preferred embodiment of the present invention is adapted for use in the treatment of a stenosis or an occlusion in a blood vessel in which the stenosis or occlusion has a length and a width or thickness which at least partially occludes the vessel's lumen. Thus, the method is effective in treating both partial and complete occlusions of the blood vessels. It is to be understood that "occlusion" as used herein, includes both complete and partial occlusions, stenoses, emboli, thrombi, plaque, and any other substance which at least partially occludes the lumen of the blood vessel.

The method of the present invention can be used to provide aspiration without the need for a separate irrigation catheter and irrigation fluid. In the context of removing plaque, thrombi or other blockages from blood vessels, it has heretofore been proposed that an isolated "chamber" surrounding the occlusion be created prior to attempting treatment, and that separate irrigation fluid be provided through an irrigation catheter to the chamber. It has been surprisingly discovered that isolation of the occlusion is not required, and that the occlusion can be successfully removed without the need for delivery of a separate irrigation catheter and irrigation fluid in those vessels where certain pressure and fluid flow conditions exist, such as saphenous vein grafts, coronary arteries, carotid arteries and other vessels.

In non-bifurcated areas of the blood vessels, it has been discovered that fluid from the collateral vessels or from the proximal portion of the same vessel acts as an infusion source. One can therefore occlude only the distal portion of the vessel to create a working area surrounding the occlusion and allow blood to flow from the proximal portion of the vessel into the working area. The area surrounding the occlusion is aspirated through the guiding catheter or aspiration catheter. It should be noted that, as used herein, "proximal" refers to the portion of the apparatus closest to the end which remains outside the patient's body, and "distal" refers to the portion closest to the end inserted into the patient's body.

Figure 15A:
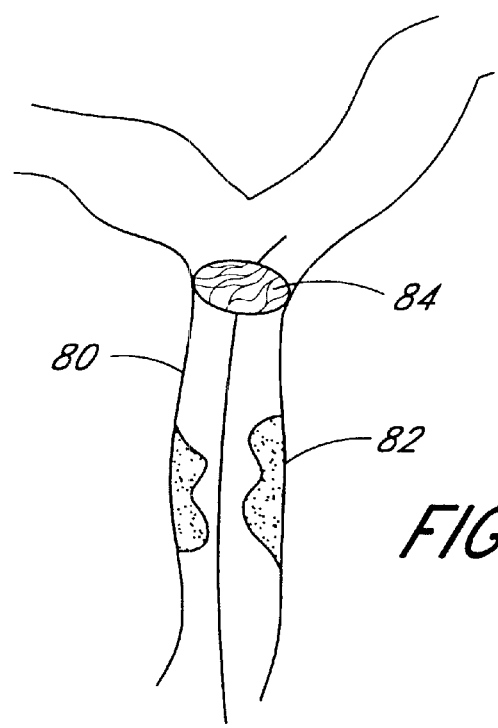
FIGS. 15A–B illustrate the positioning of the occlusive device distal to the occlusion in branching and non-branching blood vessels.
Figure 15B:
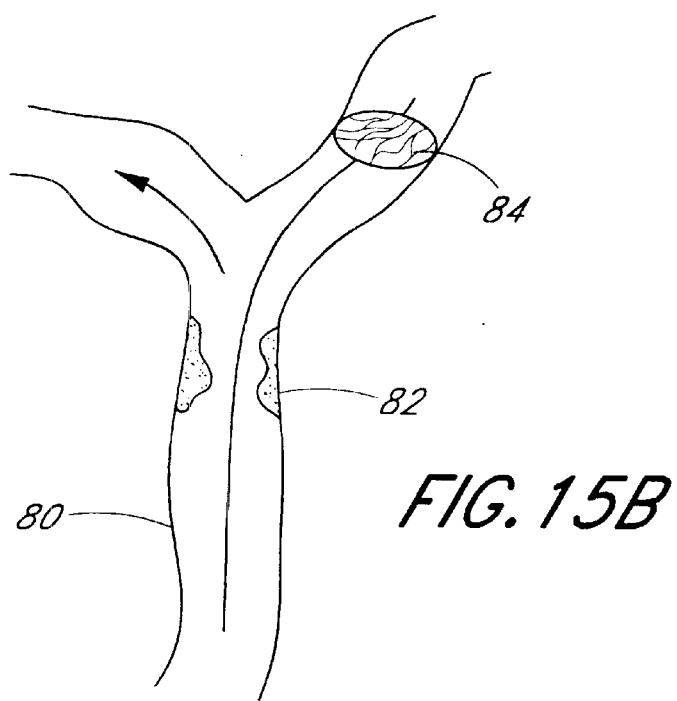

The aspiration method is adapted for use in vessels in which no bifurcation or branching occurs for a distance of approximately 2–10 cm past the site of the occlusion. Such a vessel 80 with an occlusion 82 is illustrated in FIG. 15A. This distance allows the vessel 80 to be occluded using an occlusive device 84 without the risk of any particles being carried downstream by the blood flow, where they could cause further damage (as illustrated by the arrow in FIG. 15B). There are exceptions, however; for example, the internal and external carotid arteries. Here, the common carotid artery bifurcates into the internal and external carotid arteries. It is possible to occlude the internal carotid artery only and allow particles to be carried away through the external carotid artery, since it is widely accepted that these particles can be carried safely away and will cause no damage downstream.

The aspiration method can be used in any vessel of the body where the pressure is at least 0.2 psi at any time during the diastolic/systolic cycle of the heart, and preferably, is about 1.2 psi, with a flow rate of at least 10 cc per minute. Thus, although the pressure within the vessel may fall below 0.2 psi during relaxation between heartbeats, so long as the pressure created by the heartbeat rises to at least 0.2 psi, the pressure within the vessel will be sufficient.

Figure 1:
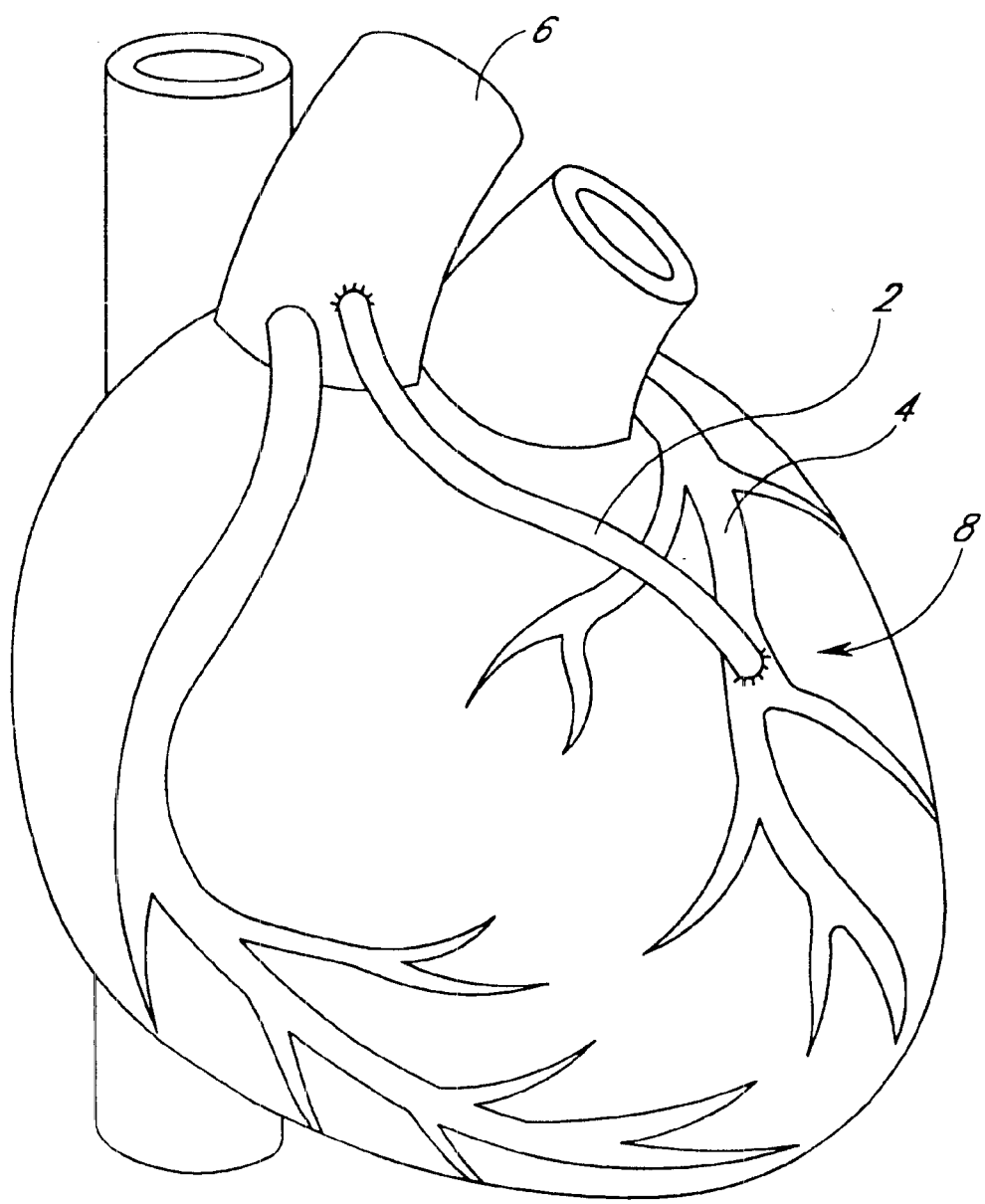
FIG. 1 is a perspective view of a human heart showing a saphenous vein graft used to bypass a portion of the coronary arteries.

A preferred embodiment of the method of the present invention is particularly suited for use in removal of occlusions from saphenous vein grafts, coronary and carotid arteries, and vessels having similar pressures and flow where a suitable working area can be created. A saphenous vein graft is depicted in FIG. 1. The graft 2 is used to bypass one of the occluded coronary arteries 4, and connects the aorta 6 to the coronary artery at a location distal the occlusion 8. Although the present invention will be described in connection with a saphenous vein graft, it should be understood that this application is merely exemplary, and the method can be used in other blood vessels as well.

Apparatus Used

Figure 12:
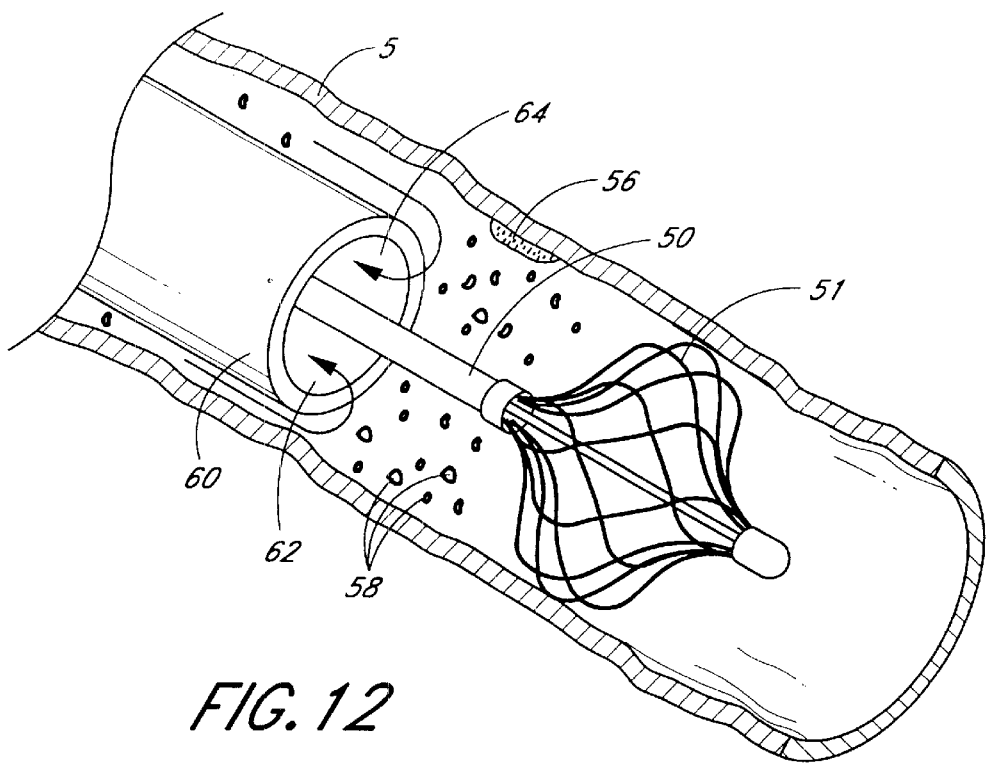
FIG. 12 is a perspective view of an over-the-wire aspiration catheter and a guidewire bearing an occlusive filter inserted into a saphenous vein graft, with the vein graft shown partially cut away.

In a preferred embodiment of the method of the present invention, a guide catheter having a single lumen is first introduced into the patient's vasculature through an incision made in the femoral artery in the groin and used to guide the insertion of other catheters and devices to the desired site. Following insertion of the guide catheter, an occlusive device is delivered to a position distal the occlusion. For example, a second catheter having an expandable device (reference numbers 51 and 52, FIGS. 9 and 12), such as an inflatable balloon, filter, expandable braid or other mechanical occlusive device, attached at its distal end is inserted through the guide catheter and past the site of the occlusion (illustrated in FIGS. 9 and 12). The expandable occlusive device should be capable of preventing the migration of particles and debris from the working area, either through total or partial occlusion of the vessel. Note that the occlusion of the vessel need not be complete. Substantial occlusion of the vessel can be sufficient for purposes of the present invention. The catheter should be sized so as to be slidable with respect to the therapy and aspiration catheters inserted over the catheter. The catheter is preferably made of metal such as stainless steel or nitinol, plastics, or composites. A guidewire having an occlusive device on its distal end is also suitable for use in the present method. The method can be effectively carried out using a number of guidewires or catheters that perform the function of occluding the vessel and allowing for the slidable insertion of various other catheters and devices. The term "catheter" as used herein is therefore intended to include both guidewires and catheters with these desired characteristics.

A preferred catheter for use to occlude the vessel is illustrated in FIGS. 10 and 11. The catheter apparatus 110 is generally comprised of four communicating members including an elongated tubular member 114, an inflatable balloon member 116, a core-wire member 120 and a coil member 122. The catheter apparatus 110 is preferably provided with an outer coating of a lubricous material, such as TEFLON.

The body member 114 of the catheter apparatus 110 is in the form of hypotubing and is provided with proximal and distal ends 114A and 114B as well as an inner lumen 115 extending along the tubular member 114. The balloon member 116 is coaxially mounted on the distal end 114B of the tubular member 114 by suitable adhesives 119 at a proximal end 116A and a distal end 116B of the balloon member 116 as in the manner shown in FIG. 11. The core-wire member 120 of the catheter 110 may be comprised of a flexible wire 120. The flexible wire 120 is joined by soldering or brazing at a proximal end 120A of the flexible wire 120 to the distal end 114B of the tubular member 114 as in the manner show in FIG. 11.

Preferably, the proximal end 120A of the flexible wire 120 has a transverse cross sectional area substantially less than the smallest transverse cross-sectional area of the inner lumen 115 of the tubular member 114. In the preferred embodiment, the flexible wire 120 tapers in the distal end 120B to smaller diameters to provide greater flexibility to the flexible wire 120. However, the flexible wire may be in the form of a solid rod or a helical coil or wire or combinations thereof.

As shown in FIG. 11, the distal end 120B of the flexible wire 120 is secured to a rounded plug 118 of solder or braze at the distal end 122B of the coil member 122. The coil member 122 of the catheter 110 may be comprised of a helical coil 122. The coil member 122 is coaxially disposed about the flexible wire 120, and is secured to the flexible wire 120 by soldering or brazing at about the proximal end 120A of the flexible wire 120 as in the manner shown in FIG. 11.

The balloon member 116 is preferably a compliant balloon formed of a suitable elastic material such as a latex or the like. The flexible coil 122 is preferably formed of a wire of platinum based alloys. The flexible core-wire 120 and the tubular member 114 are preferably formed of a nickel-titanium alloy.

Alternatively, the occlusion catheter can be configured so as to allow for aspiration through the catheter, thus eliminating the need for a separate aspiration catheter. In this embodiment, the catheter has a long hollow shaft, having an outer diameter of less than about 0.038", and preferably about 0.025" to about 0.035". The inner diameter or lumen of the shaft is about 0.020" to about 0.030". Aspiration occurs through the inner diameter of the catheter. The catheter has an occlusive device attached to its distal end. The occlusive device is preferably a mechanical device such as a self-expanding braid or coil which acts as a filter, preventing particles from moving downstream. The catheter shaft further comprises at least one opening, and preferably several openings, located just proximal to the occlusive device, which allow for aspiration. The proximal end of the catheter is adapted to allow a source of negative pressure to be attached, such that it is in fluid communication with the inner lumen.

Once the guiding catheter and catheter have been properly positioned inside the vessel, the occlusive device at the distal end of the catheter is actuated to occlude the vessel distal to the existing occlusion. A therapy catheter then is delivered to the site of the occlusion. The term "therapy catheter" is meant to include any of a number of known devices used to treat an occluded vessel. For example, a catheter carrying an inflatable balloon for use in balloon angioplasty can be delivered to dilate the occlusion. Thermal balloon angioplasty includes the use of heat to "mold" the vessel to the size and shape of the angioplasty balloon. Similarly, an intravascular stent can be delivered via a balloon catheter and deployed at the site of the occlusion to keep the vessel open. Cutting, shaving, scraping or pulverizing devices can be delivered to excise the occlusion in a procedure known as atherectomy. A laser or ultrasound device can also be delivered and used to ablate plaque in the vessel. Various thrombolytic or other types of drugs can be delivered locally in high concentrations to the site of the occlusion. It is also possible to deliver various chemical substances or enzymes via a catheter to the site of the stenosis to dissolve the obstruction. The term "therapy catheter" encompasses these and similar devices.

After the therapy has been performed and the occlusion has been removed using any of the methods and apparatus described above, the area is aspirated to remove fluid and debris. Aspiration can be provided through the guide catheter if desired. A source of negative pressure is attached at the proximal end of the guide catheter, and fluid and debris are aspirated through the guide catheter's main lumen. Alternatively, an aspiration catheter or similar debris removing device is used to remove particles and any other debris. The term "aspiration catheter" includes any device which creates an area of fluid turbulence and uses negative pressure to aspirate fluid and debris, and includes thrombectomy catheters, rheolitic devices and those devices which create a venturi effect within the vessel. Thus, it is possible that a single catheter is used as both the therapy catheter and the aspiration catheter. It should be noted that any particles which break free during therapy and aspiration procedures will be kept at the site of the procedure by the occlusive device occluding the distal portion of the vessel in combination with the fluid pressure coming from the proximal portion of the vessel. The debris is prevented from migrating elsewhere, and remains localized for removal by aspiration.

Figure 2:
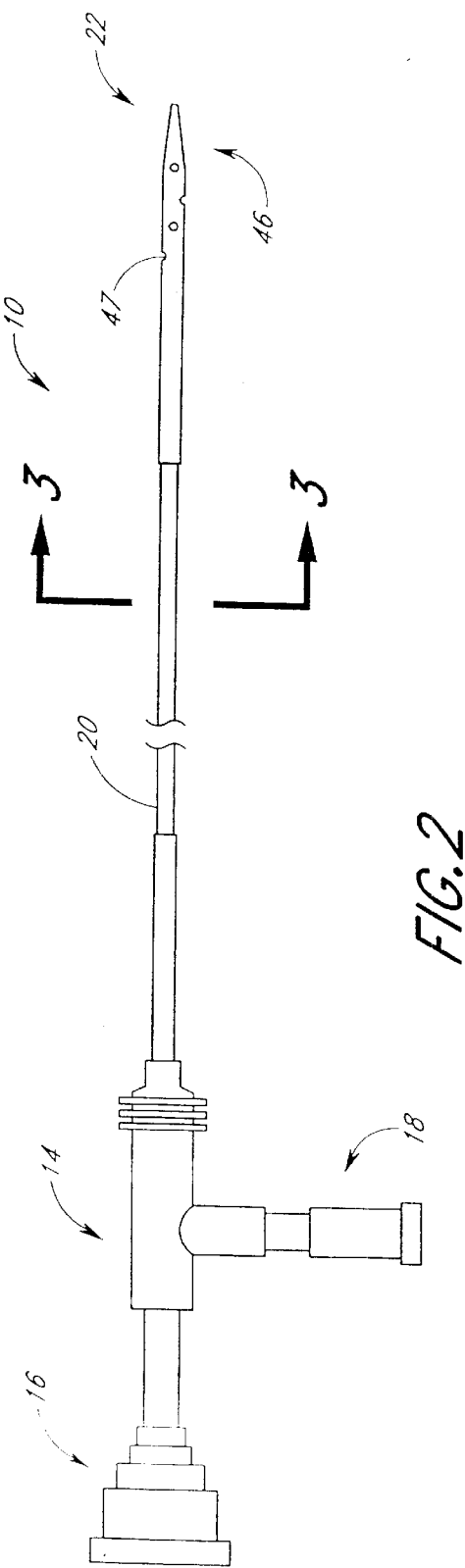
FIG. 2 is a side view of an over-the-wire aspiration catheter in accordance with the present invention.

An aspiration catheter particularly suited for use in the method described is illustrated in FIG. 2. The catheter 10 includes an adaptor 14 and a seal 16 at its proximal end. The catheter 10 further includes an aspiration port 18 to which a source of negative pressure is attached. The aspiration catheter further comprises a long hollow shaft 20 having a distal end 22. The distal tip 22 can include a radiopaque marker to aid in locating the tip 22 during insertion into the patient, and is preferably soft to prevent damage to the patient's vasculature.

Figure 4:
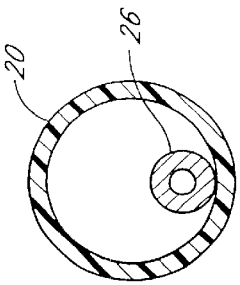
FIG. 4 is a cross section of the aspiration catheter of FIG. 2 showing a guide wire over which the aspiration catheter rides.
Figure 3:
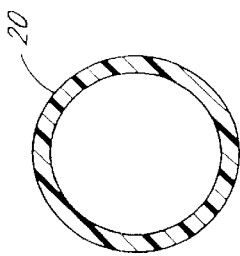
FIG. 3 is a cross section of the aspiration catheter of FIG. 2, taken along line 3—3 in FIG. 2.

The aspiration catheter illustrated in FIG. 2 is an over-the-wire catheter. As seen in FIG. 3, the catheter shaft 20 is hollow. During insertion of the aspiration catheter 10, the proximal end of a guidewire 26 is inserted into the distal end of the aspiration catheter 22, and the aspiration catheter 10 is slidably advanced over the guidewire 26, which is positioned inside the hollow lumen 24 of the aspiration catheter 10. The position of the guidewire 26 relative to the shaft 20 of the aspiration catheter 10 is illustrated in FIG. 4, but of course can vary. For this type of aspiration catheter 10, a very long guidewire 26, generally around 300 cm in length, is used to facilitate the insertion of the aspiration catheter 10 over the guidewire 26.

Figure 5:
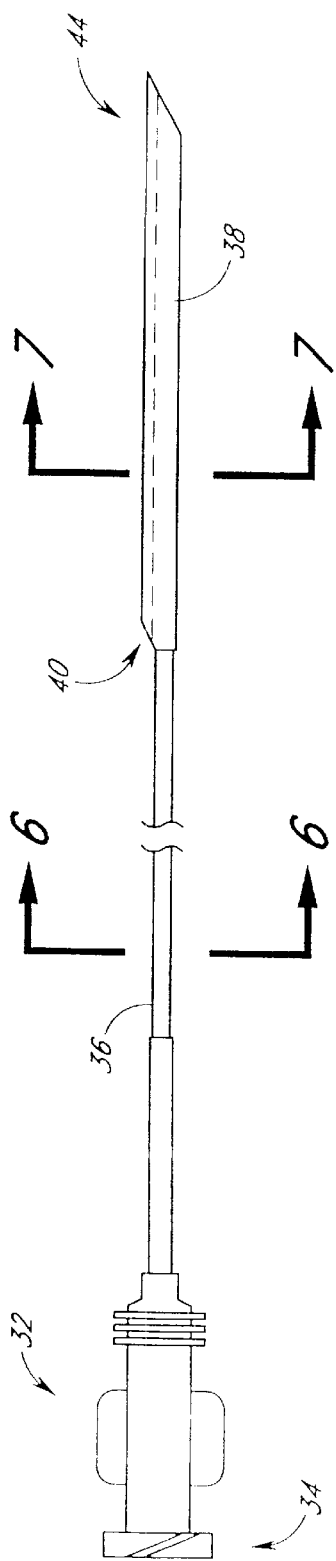
FIG. 5 is a side view of a single operator type aspiration catheter in accordance with the present invention.
Figure 7B:
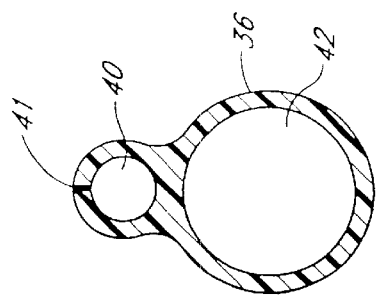
FIG. 7 is a cross section of the distal end of the aspiration catheter of FIG. 5, taken along line 7—7 of FIG. 5.
Figure 7A:
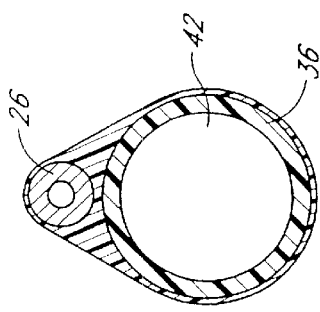
Figure 6:
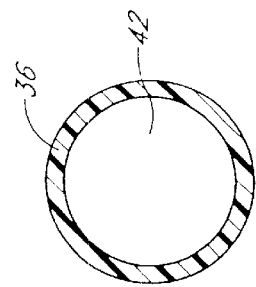
FIG. 6 is a cross section of the proximal end of the aspiration catheter of FIG. 5, taken along line 6—6 of FIG. 5.

Alternatively, the aspiration catheter 30 can be of a single operator design, as illustrated in FIGS. 5–7. The catheter 30 has an adaptor 32 and an aspiration port 34 at its proximal end. Like the over-the-wire aspiration catheter 10, the single operator aspiration catheter 30 further comprises a long hollow shaft 36 having a distal end 38. The distal tip 38 can include a radiopaque marker to aid in locating the tip 38 during insertion into the patient, and is preferably soft to prevent damage to the patient's vasculature. At the distal end of the shaft 38, a guidewire lumen 40 is attached. This lumen 40 provides a separate lumen, apart from the main aspiration lumen 42 of the catheter 30, for the insertion of the guidewire 26. This guidewire lumen can be as short as 5 cm. As illustrated in FIG. 7A, during delivery of the aspiration catheter 30, the proximal end of the guidewire 26 is inserted into the distal end of the guidewire lumen 40, and the guidewire lumen 40 is slidably advanced over the guidewire 26. Unlike the over-the-wire catheter 10 described above, only a short segment of the single operator aspiration catheter 30 rides over the guidewire 26, and the guidewire 26 remains in the guidewire lumen 40 and does not enter the aspiration lumen 42 of the aspiration catheter 30. With the single operator system 30, the long guidewire 26 used with the over-the-wire catheter 10, and the extra operator needed to handle it, are not required.

Although the guidewire lumen 40 is shown in FIG. 5 as being located only on the distal end 38 of the shaft of the aspiration catheter 36, the lumen 40 can also be made to extend the entire length of the shaft 36 if desired. In both embodiments, the aspiration lumen 42 is advantageously left completely unobstructed to provide more efficient aspiration. The guidewire lumen 40 can also include a slit in the outside wall of the lumen to facilitate faster and easier insertion and removal of the guidewire 26 through the side wall of the lumen, as shown in FIG. 7B.

In another embodiment not shown, the aspiration catheter can be configured such that the therapy catheter can be inserted through the lumen of the aspiration catheter. The aspiration lumen is made large enough to accommodate the desired therapy catheter. This allows the aspiration catheter and the therapy catheter to be delivered into the patient at the same time. When therapy is complete, the therapy catheter is removed while the aspiration catheter remains in place. This eliminates the need to separately deliver the aspiration catheter after removal of the therapy catheter, saving valuable time. It is preferable that the size of the guide catheter used during this type of procedure be sized from at least 8 to about 10 French to accommodate the size of the "over-the-therapy-catheter" aspiration catheter.

In yet another embodiment, also not shown, the therapy catheter can be built over the aspiration catheter. For example, a dual-lumen catheter having a dilatation balloon at its distal end can be used. One lumen is used to inflate the dilatation balloon to be used for angioplasty, while the second lumen is used for aspiration. This design allows a single combined aspiration catheter and therapy catheter to be delivered into the patient. When therapy is complete, aspiration is carried out without the need to first remove the therapy catheter.

In the embodiment where the occlusion catheter is adapted to allow aspiration therethrough, no separate aspiration catheter is required. Once the occlusive device on the catheter is positioned distal to the occlusion, the occlusive device is activated to at least partially occlude the vessel. A therapy catheter is delivered and therapy performed on the occlusion. Once therapy is complete, a source of negative pressure is provided at the proximal end of the occlusion catheter, and aspiration occurs through the openings at the distal end of the catheter, just proximal to the occlusive device. Aspiration is therefore accomplished without the need for a separate aspiration catheter, or removal of the therapy catheter.

Figure 8A:
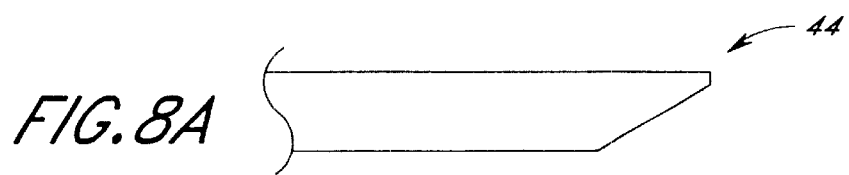
FIGS. 8A–C are side views of the various embodiments of the distal end of the aspiration catheter of the present invention.
Figure 8B:
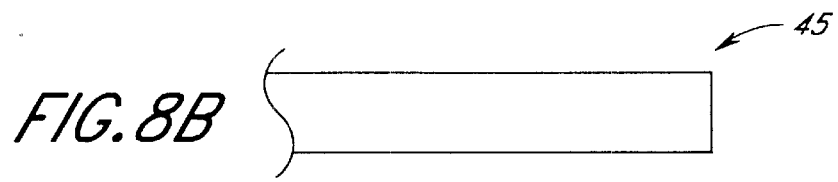
Figure 8C:
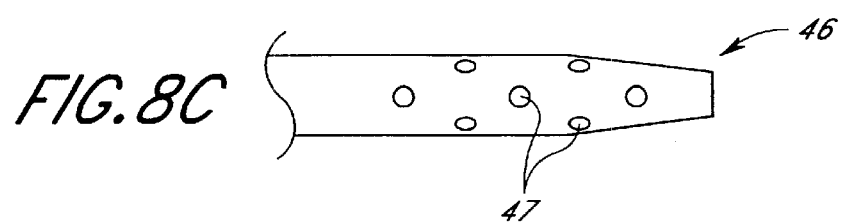

FIGS. 8A, 8B, and 8C illustrate various embodiments of the distal end of the aspiration catheter. FIG. 8A shows the preferred tip 44, wherein the end has been angled. This tip 44 is also shown in FIG. 5. This angled tip 44 maximizes the area of aspiration. The distal tip of the aspiration catheter can also be blunt 45, as shown in FIG. 8B, or can be tapered 46, with holes along the tip 47 to provide for aspiration, as illustrated in FIGS. 8C and 2.

Additional details relative to the catheters described above and their use are found in copending application Ser. No. 08/812,876, filed Mar. 6, 1997, entitled "Hollow Medical Wires and Methods of Constructing Same, now U.S. Pat. No. 6,068,623, application Ser. No. 08/858,900, filed May 19, 1997, entitled "Catheter for Emboli Containment System", application Ser. No. 09/026,013, filed Feb. 19, 1998, entitled "Aspiration System and Method", now U.S. Pat. No. 6,152,909, application Ser. No. 09/026,225, filed Feb. 19, 1998, entitled "Balloon Catheter and Method of Manufacture", application Ser. No. 09/025,991, filed Feb. 19, 1998, entitled "Syringe and Method for Inflating Low Volume Catheter Balloons", abandoned, application Ser. No. 09/026,106, filed Feb. 19, 1998, entitled "Occlusion of a Vessel", now U.S. Pat. No. 6,312,407, application Ser. No. 08/975,723, filed Nov. 20, 1997, entitled "Low Profile Catheter Valve and Inflation Adaptor", now U.S. Pat. No. 6,050,972, and application Ser. No. 09/049,712, filed Mar. 27, 1998, entitled "Exchange Method for Emboli Containment", all of which are hereby incorporated by reference in their entirety.

Method

The method of the present invention as used to remove plaque and any associated thrombi from a saphenous vein graft is described below in connection with FIG. 9. Again, it should be noted that this application is merely exemplary, and that the method of the present invention can be used in other blood vessels and to remove other types of occlusions as well.

A guide catheter (not shown) is introduced into the patient's vasculature through an incision in the femoral artery in the groin of the patient. The guide catheter has a single large lumen, and is used to guide the insertion of other catheters and devices. The guide catheter is advanced until it reaches the aorta and the ostium of the vein graft, where it will remain in place throughout the procedure. Fluoroscopy is typically used to guide the guide catheter and other devices to the desired location within the patient. The devices are frequently marked with radiopaque markings to facilitate visualization of the insertion and positioning of the devices within the patient's vasculature. It should be noted that at this point, blood is flowing through the vessel in a proximal to distal direction.

Next, an occlusive device is delivered to a site distal the occlusion. For example, a catheter or guidewire 50 having an occlusive device at its distal end is delivered through the guide catheter into the saphenous vein graft 5 and past the site of the occlusion 56. In this example, the occlusive device is an inflatable balloon 52. The balloon 52 is inflated to occlude the vein graft 5 at a site distal to the occlusion 56 to create a working area surrounding the occlusion. By "working area" is meant an area extending from the occlusive device in a proximal direction for a distance up to about 20 cm. The blood coming from the aorta enters the saphenous vein graft 5 and keeps any particles 58 dislodged during the procedure from flowing proximally. In addition, the blood pressure and flow coming from the aorta provides the irrigation necessary for aspiration. As noted above, the blood pressure in the vessel is preferably at least about 0.2 psi, and the flow rate is at least about 10 cc per minute at some point during the diastolic/systolic cycle of the heart.

Figure 13:
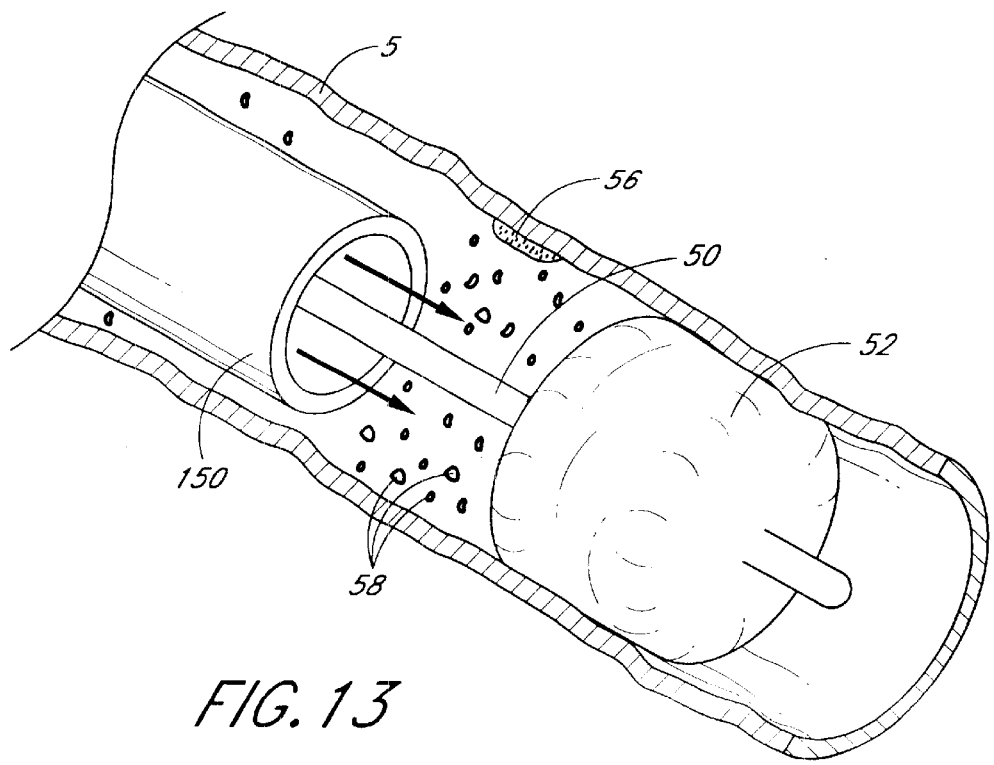
FIG. 13 is a perspective view of a therapy catheter delivering a drug and a guidewire having on occlusive device inserted into a saphenous vein graft, with the vein graft shown partially cut away.

Once the vein 5 is occluded, a therapy catheter 150, as illustrated in FIG. 13, is delivered, if desired. The therapy catheter can be any of a number of devices, including a balloon catheter used to perform angioplasty, a catheter which delivers a stent, a catheter for delivering enzymes, chemicals, or drugs to dissolve and treat the occlusion (as illustrated in FIG. 13), an atherectomy device, or a laser or ultrasound device used to ablate the occlusion. Alternatively, the therapy catheter can be eliminated and use of the guide catheter or a separate aspiration catheter alone can be used to aspirate the occlusion. This method is especially useful to remove emboli from the coronary arteries following acute myocardial infarction, because the aspiration catheter can be made small enough to enter the coronary arteries.

Once the desired therapy is performed, the therapy catheter is withdrawn from the patient's body and an aspiration catheter 60 is delivered over the guidewire 50 and through the guiding catheter. The aspiration catheter 60 rides over the guidewire 50 with the guidewire 50 inserted through the aspiration lumen 62 of the catheter 60. Alternatively, a single operator type aspiration catheter can be used, in which only a portion of the aspiration catheter rides over the guidewire, which is inserted into a separate guidewire lumen. FIG. 9 illustrates the treatment site during delivery of the over-the-wire aspiration catheter 60 into the saphenous vein graft 5.

Figure 14A:
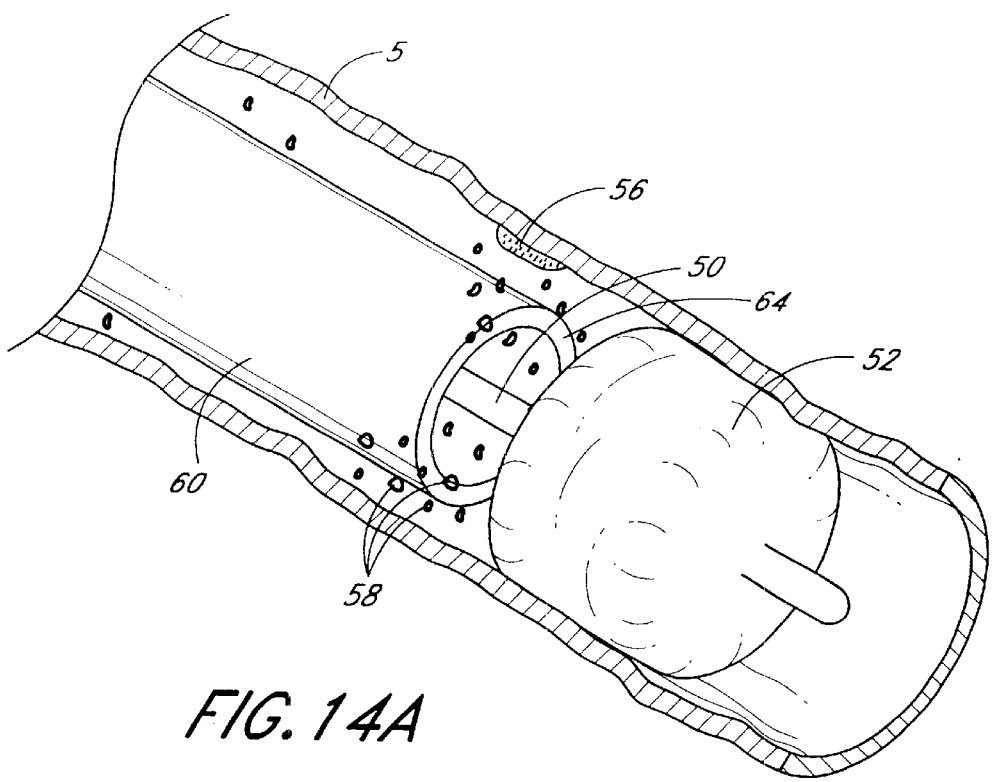
FIGS. 14A–D show a perspective view of the movement of an over-the wire aspiration catheter during aspiration in a saphenous vein graft, with the vein graft shown partially cut away.
Figure 14B:
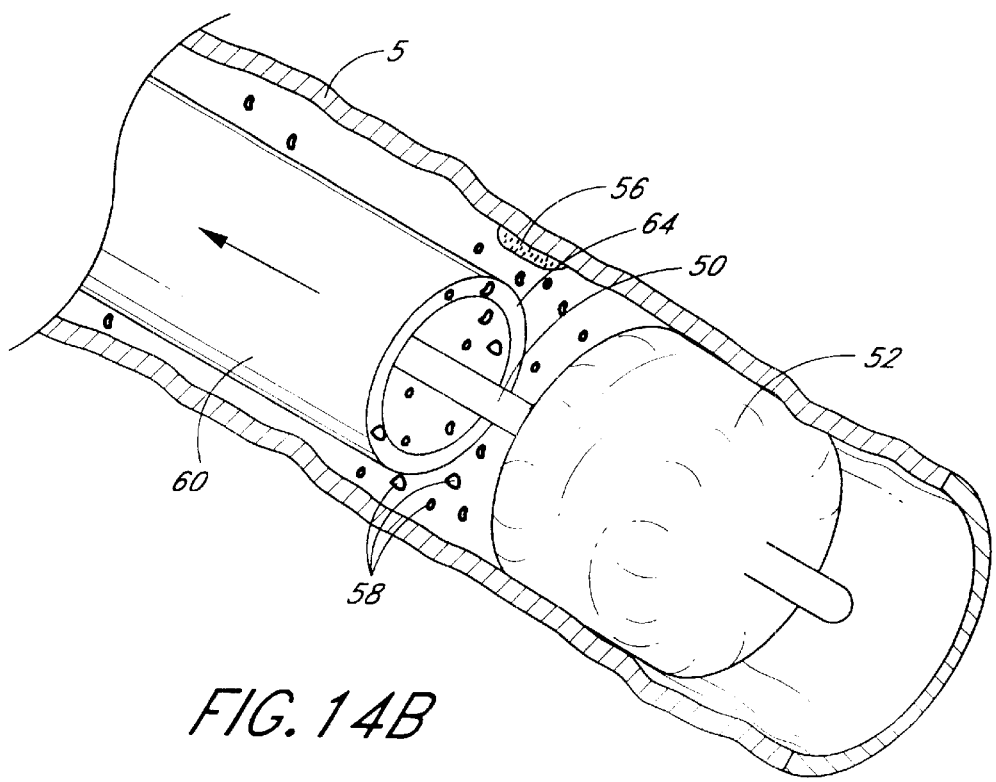
Figure 14C:
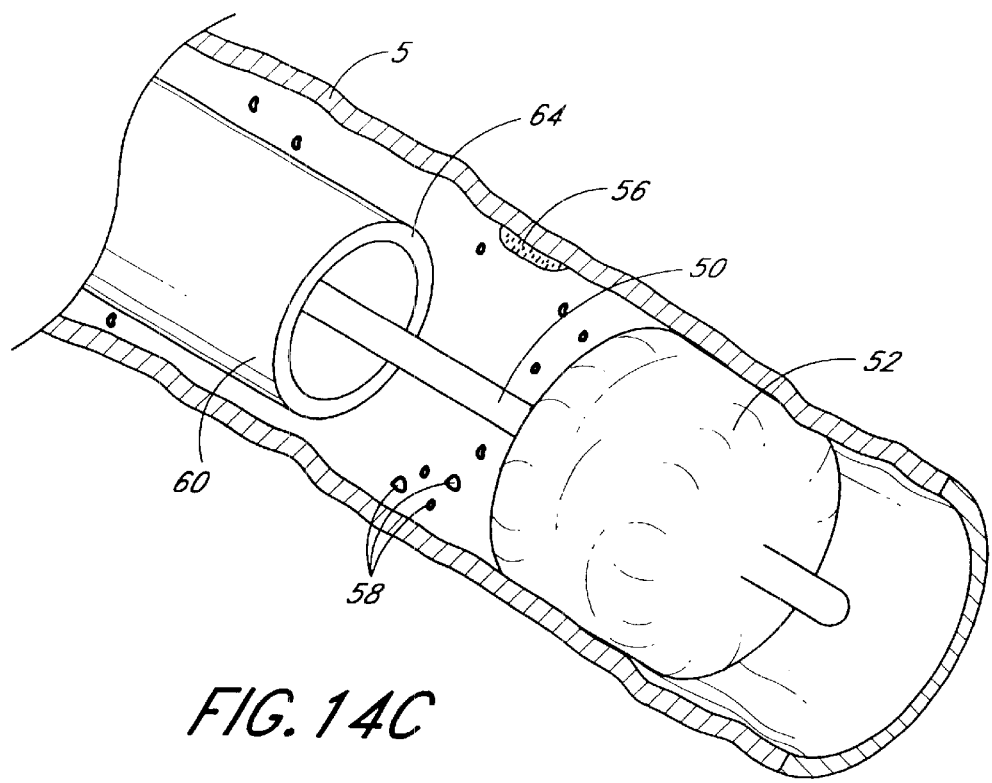
Figure 14D:
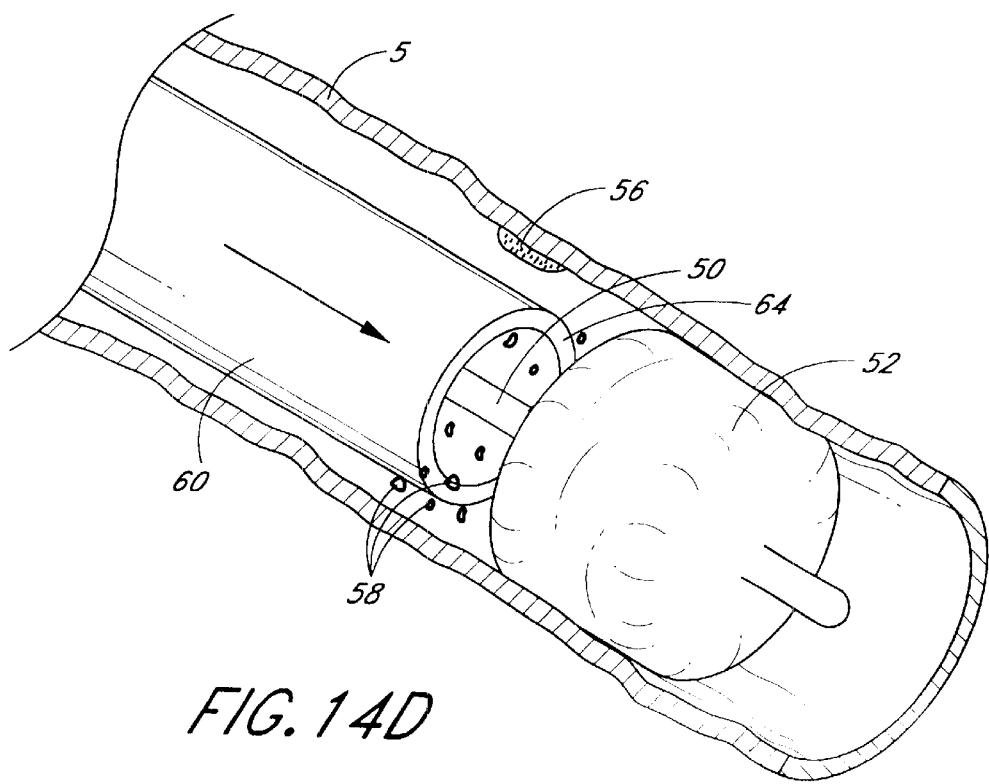

The treatment site during the aspiration procedure is illustrated in FIGS. 14A–D. The distal tip of the aspiration catheter 64 crosses the site of the occlusion 56 and is initially positioned distal to the occlusion 56 and as close to the occlusive balloon 52 as possible, preferably less than about 5 cm, and more preferably less than about 2 cm, from the proximal side of the balloon 52 (FIG. 14A). Thus, in one embodiment, the distal tip of the aspiration catheter 64 is initially positioned immediately adjacent the occlusive balloon 52. Aspiration is begun, and the operator moves the aspiration catheter in a proximal direction, crossing the site of the occlusion 56 and increasing the distance between the distal tip 64 of the catheter and the occlusive balloon 52 (FIGS. 14B and 14C). During aspiration, the distal tip of the aspiration catheter 64 moves in a direction proximal to the balloon 52, crossing the occlusion 56, and continuing in a proximal direction for a distance that is preferably at least 1 cm proximal to the site of the occlusion 56. The distal tip of the aspiration catheter 64 may continue to be moved in a proximal direction away from the occlusion 56 for up to 10 cm or more, or until the tip 64 reaches the guide catheter. Aspiration can therefore occur anywhere between about 0 to 20 cm proximal to the occlusive device 52. During aspiration, the flow of fluid within the vessel is in a proximal to distal direction, while fluid flow within the lumen of the catheter is in a distal to proximal direction. If desired, the distal tip of the aspiration catheter 64 is then again advanced across the occlusion 56 in the distal direction until it is again just immediately adjacent to the occlusive balloon 52 (FIG. 14D). This movement of the tip of the aspiration catheter 64 in a proximal and distal direction can be repeated more than once to ensure complete aspiration of all debris.

In an alternate embodiment, the distal tip of the catheter 64 is initially positioned proximal to the occlusion 56, preferably at least 1 cm proximal to the occlusion 56. Aspiration is begun, and the distal tip of the catheter 64 is advanced in a distal direction across the occlusion 56 until the tip 64 is positioned immediately adjacent to the occlusive balloon 52. The tip of the catheter 64 is then moved in a proximal direction, back across the occlusion 56. Preferably, the tip of the catheter 64 continues in a proximal direction for a distance that is preferably at least 1 cm proximal to the site of the occlusion 56. As described above, the distal tip of the aspiration catheter 64 can continue to be moved in a proximal direction away from the occlusion 56 for up to 10 cm or more, or until the tip 64 reaches the guide catheter. This movement of the tip of the catheter 64 in a distal and proximal direction can be repeated as often as desired to ensure complete removal of particles and debris.

Figure 9:
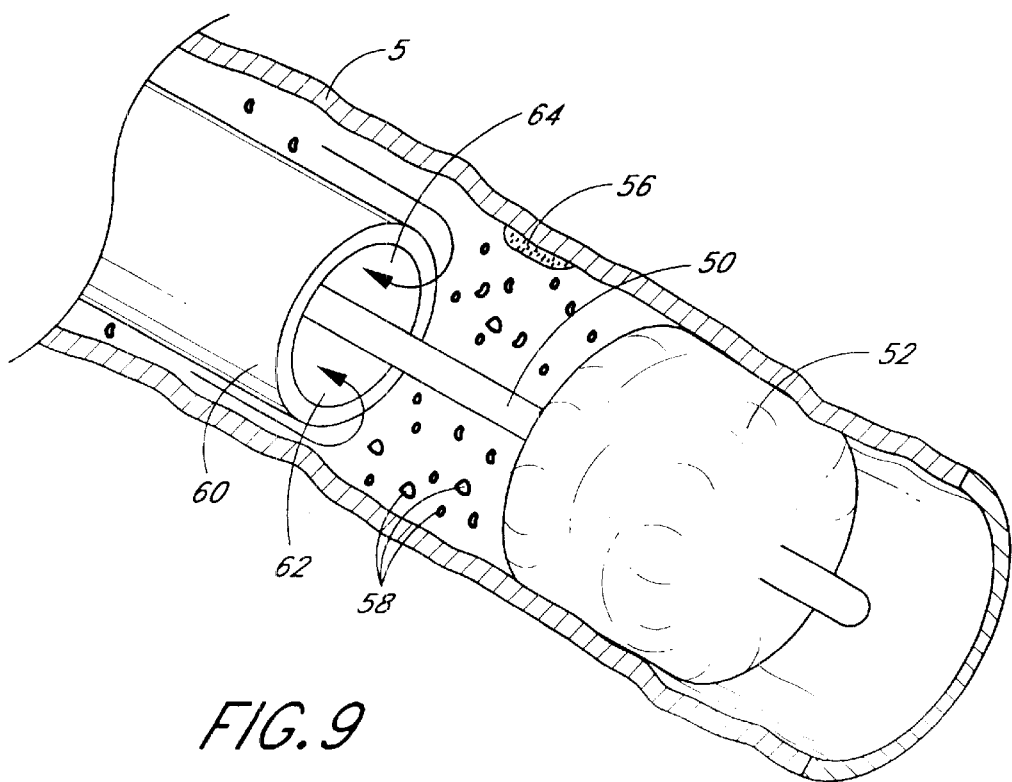
FIG. 9 is a perspective view of an over-the-wire aspiration catheter and guidewire inserted into a saphenous vein graft in accordance with the present invention, with the vein graft shown partially cut away.

The blood flow supplied by the aorta will move any particles 58 from a position proximal to the distal tip of the aspiration catheter 64, thus allowing them to be aspirated, as illustrated by the arrows in FIG. 9. If a particle, however, is too far distal to the tip of the aspiration catheter 64 (for example, more than about 2 cm), the blood pressure will keep it there and not allow it to aspirated from the vessel 5. The aspiration pressure can be increased, but not without the risk of severely damaging the vessel. Rather, this distal and proximal movement of the aspiration catheter, including placement of the tip immediately adjacent the occlusive balloon, will allow the user to completely capture these distal particles. In addition, once aspiration has begun, additional blood will flow into the area adjacent and distal to the tip of the aspiration catheter, creating turbulence and allowing for the complete removal of debris.

A preferred source of negative pressure is any rigid container containing a fixed vacuum, such as a syringe, attached to the proximal end of the aspiration catheter at the aspiration port 34 (see FIG. 5). A mechanical pump or bulb or any other appropriate source of negative pressure can also be used. The difference between the existing pressure within the vessel and the aspiration pressure within the vessel should not exceed about 50 psi. As noted above, if too much aspiration pressure is applied, the change in pressure in the vessel will be too great and damage may occur to the vessel itself.

After the area inside the graft 5 is aspirated to remove any particles 58 or other debris, the aspiration catheter 60 is removed. The balloon 52 is deflated and the guidewire 50 and guiding catheter are removed.

As described above, the aspiration catheter can be sized such that it can receive the therapy catheter within its lumen or the therapy catheter can be built over the aspiration catheter. In either case, the aspiration catheter and the therapy catheter are delivered over the guidewire and into the vein graft together. When therapy is complete, the therapy catheter can be removed if desired while the aspiration catheter remains in place. When aspiration is complete, the aspiration catheter, guidewire and guiding catheter are removed from the patient's body. Delivering the aspiration catheter and therapy catheter together saves time, which is critical during these types of procedures. Alternatively, the guide catheter can be used to provide aspiration through its main lumen.

In yet another embodiment, aspiration takes place through the lumen of the occlusion catheter or guidewire. The occlusive device on the catheter is positioned distal to the occlusion, and the occlusive device is activated to at least partially occlude the vessel. The therapy catheter is delivered and therapy performed. A source of negative pressure is provided at the proximal end of the occlusion catheter, and aspiration occurs through openings located at the distal end of the catheter just proximal to the occlusive device. This eliminates the need for a separate aspiration catheter, and the need to remove the therapy catheter prior to aspiration. Again, this saves time, which is critical during these types of procedures.

While the foregoing detailed description has described several embodiments of the apparatus and methods of the present invention, it is to be understood that the above description is illustrative only and not limiting of the disclosed invention. It will be appreciated that the specific dimensions of the various catheters and guidewires can differ from those described above, and that the methods described can be used within any biological conduit within the body and remain within the scope of the present invention. Thus, the invention is to be limited only by the claims which follow.

What is claimed is:

1. A method of treatment of a blood vessel in which blood fluid flows proximally to distally, said method comprising:

delivering a guidewire having a proximal end and a distal end and an expandable device thereon into the blood vessel, said expandable device being actuatable between a nonexpanded state and an expanded state, said expandable device when in said expanded state forming a barrier sufficient to inhibit emboli suspended in said fluid from migrating past the barrier in a proximal to distal direction;

preventing emboli from moving in a distal to proximal direction by exposing said expandable device to blood fluid pressure within said vessel;

advancing a catheter having a lumen in fluid communication with a distal opening in the catheter, said advancing comprising moving said distal opening relative to said expandable device within the blood vessel such that said opening is distal to at least a portion of an occlusive substance within said blood vessel, said occlusive substance comprising said emboli suspended in said fluid; and drawing fluid from the vessel into the distal opening such that (a) a fluid flow is created in the lumen in a distal to proximal direction, and (b) said fluid flow is simultaneously created in said vessel in a proximal to distal direction, whereby said emboli are carried by said fluid flow from said vessel into said distal opening and through said lumen of said catheter.

2. The method of claim 1, wherein the occlusive substance includes material on a wall of the vessel.

3. The method of claim 2, wherein said advancing comprises moving said distal opening such that said distal opening is distal to at least some of the material on the wall of the vessel.

4. The method of claim 1, further comprising moving the distal opening in the catheter relative to the expandable device during said drawing of fluid.

5. The method of claim 1, wherein said expandable device is an inflatable balloon.

6. The method of claim 1, wherein said expandable device is a filter.

7. The method of claim 1, further comprising advancing a guide catheter until a distal end of the guide catheter is positioned proximal to the emboli, and wherein said catheter is advanced through said guide catheter.

8. The method of claim 1, wherein said blood vessel comprises a saphenous vein graft.

9. The method of claim 8, wherein said fluid pressure is provided by blood from the aorta.

10. The method of claim 1, wherein said blood vessel comprises a carotid artery.

11. The method of claim 1, wherein the emboli are located in a segment of the blood vessel having substantially no side branches.

12. The method of claim 1, wherein the catheter is advanced over the guidewire.

13. A method for the evacuation of emboli from a blood vessel comprising:

positioning an expandable device distal to a location in the vessel having an occlusion on the walls of said vessel;

positioning a catheter having a lumen in fluid communication with a distal opening in the catheter such that said opening is distal to said location;

drawing fluid from the vessel into the distal opening such that emboli broken off from said occlusion are carried by said fluid from said vessel into said distal opening and through said lumen of said catheter; and moving the distal opening in the catheter until it is proximal to said location during the drawing of fluid into the distal opening.

14. The method of claim 13, wherein positioning said expandable device further comprises delivering a guidewire into said vessel, said guidewire carrying said expandable device.

15. The method of claim 14, wherein said catheter is positioned in the blood vessel over said guidewire.

16. The method of claim 13, further comprising actuating said expandable device into an expanded position prior to drawing fluid from the vessel.

17. The method of claim 13, wherein said drawing fluid further comprises creating a fluid flow in the lumen in a distal to proximal direction, and simultaneously creating fluid flow in the vessel in a proximal to distal direction.

18. The method of claim 13, wherein the distal opening in the catheter is positioned distal said location more than once during the drawing of fluid.

19. The method of claim 13, wherein said expandable device is an inflatable balloon.

20. The method of claim 13, wherein said expandable device is a filter.

21. The method of claim 13, further comprising, prior to drawing fluid into the distal opening of the catheter, performing therapy on the occlusion, the performing of therapy causing emboli to break off from the occlusion.

22. A method for the treatment of an occlusion in a blood vessel having a fluid pressure of at least 0.2 psi, comprising:

inserting a guidewire having an occlusive device at its distal end into said blood vessel, until said occlusive device is distal to said occlusion;

activating said occlusive device to at least partially occlude said vessel distal to said occlusion and create a working area around said occlusion;

advancing a therapy catheter into said blood vessel until it reaches said occlusion;

performing therapy on said occlusion;

utilizing fluid pressure within said vessel to inhibit particles produced during therapy from substantial migration in a direction proximal to said occlusion;

removing said therapy catheter;

delivering an aspiration catheter having a proximal end and a distal end over said guidewire until the distal end of said aspiration catheter is at a location proximal to the occlusive device and distal to the occlusion;

creating a flow of fluid within said vessel in a proximal to distal direction by aspirating fluid from said working area inside the vessel through said distal end of said aspiration catheter, whereby said particles are removed from the working area and said fluid pressure provides fluid to replace fluid aspirated from the working area; and deactivating said occlusive device and removing said catheter.

23. The method of claim 22, wherein said aspiration catheter comprises a hollow lumen and a separate second lumen for receiving said guidewire, and wherein said aspiration catheter is delivered by inserting a proximal end of said guidewire into said second lumen, and slidably advancing said second lumen of said aspiration catheter over said guidewire.

24. The method of claim 22, wherein said distal end of said aspiration catheter is inserted at least one time to a position no more than about 5 cm proximal to said occlusive device and thereafter slidably withdrawn in a proximal direction.

25. The method of claim 22, wherein said blood vessel is selected from the group consisting of a saphenous vein graft, a coronary artery, and a vessel above the aortic arch.

26. The method of claim 22, wherein said blood vessel has a fluid flow rate of at least about 10 cc per minute.

27. The method of claim 22, wherein said blood vessel has a fluid flow rate of from about 60 to about 80 cc per minute.

28. The method of claim 22, further comprising inserting a guide catheter to aid in the insertion of said occlusive device and said guidewire.

29. The method of claim 22, wherein activating said occlusive device results in the vessel being substantially occluded.

30. The method of claim 22, wherein said occlusive device is a balloon and said activating step comprises inflating said balloon.

31. The method of claim 22, wherein said occlusive device is a filter and said activating step comprises deploying said filter to prevent migration of particles downstream.

32. The method of claim 22, wherein performing said therapy comprises delivering a drug directly to the site of said occlusion.

33. The method of claim 22, wherein performing said therapy comprises creating a venturi effect within said vessel to aspirate said occlusion, and wherein the fluid aspiration occurs simultaneously.

34. The method of claim 22, wherein performing said therapy comprises creating fluid turbulence within said vessel to aspirate said occlusion, and wherein the fluid aspiration occurs simultaneously.

35. The method of claim 22, wherein said therapy catheter is selected from the group consisting of a thrombectomy catheter, a rheolitic device, and a device which creates a venturi effect within the vessel, and wherein the therapy and the fluid aspiration are performed simultaneously.

36. The method of claim 22, further comprising moving the distal end of the aspiration catheter within said working area during aspiration.

37. The method of claim 36, wherein the distal end of the aspiration catheter is moved in a distal to proximal direction during aspiration.

38. The method of claim 36, wherein the distal end of the aspiration catheter is moved in a proximal to distal direction during aspiration.

39. The method of claim 22, wherein the emboli are located in a segment of the blood vessel having substantially no side branches.

40. A method of treatment of a blood vessel in which blood flows proximally to distally at a location having an occlusion on the walls of said vessel that constricts said vessel, said method comprising:
   delivering a guidewire having a proximal end and a distal end and an expandable device thereon into the blood vessel, said expandable device being actuatable between a nonexpanded state and an expanded state, said expandable device when in said expanded state forming a barrier sufficient to inhibit emboli in said blood from migrating past the barrier in a proximal to distal direction;
   preventing emboli from moving in a distal to proximal direction by exposing said expandable device to blood flowing in a proximal to distal direction;
   advancing a catheter having a lumen in fluid communication with a distal opening in the catheter, said advancing comprising moving said distal opening relative to said expandable device within the blood vessel such that said opening is distal to said occlusion within said blood vessel; and
   drawing blood from the vessel into the distal opening such that (a) a blood flow is created in the lumen in a distal to proximal direction, and (b) said blood flow is simultaneously created in said vessel in a proximal to distal direction, whereby said emboli are carried by said blood flow from said vessel into said distal opening and through said lumen of said catheter.

41. The method of claim 40, wherein said advancing comprises moving said distal opening such that said opening is distal to at least some of the emboli.

42. The method of claim 40, further comprising moving the distal opening in the catheter in a distal to proximal direction during said drawing of blood to cross at least a portion of the occlusion.

43. The method of claim 40, wherein said expandable device is an inflatable balloon.

44. The method of claim 40, wherein said expandable device is a filter.

45. The method of claim 40, wherein said catheter is advanced over the guidewire.

46. The method of claim 40, further comprising, prior to drawing blood into the distal opening of the catheter, performing therapy on the occlusion, the performing of therapy causing emboli to break off from the occlusion.

47. A method for the evacuation of emboli from a blood vessel in which therapy has been performed on a lesion in the vessel, comprising:
   positioning a catheter having a lumen in fluid communication with a distal opening in the catheter such that said opening is in the region of said emboli;
   drawing fluid from the vessel into the distal opening such that emboli are carried by said fluid flow from said vessel into said distal opening and through said lumen of said catheter; and
   moving the distal opening in the catheter relative to said lesion while continuing to draw fluid into the distal opening.

48. The method of claim 47, wherein the distal opening in the catheter is positioned at a location distal to at least a portion of an occlusive substance within said blood vessel.

49. The method of claim 48, wherein the occlusive substance comprises emboli.

50. The method of claim 48, wherein the occlusive substance includes material that is attached to the walls of the blood vessel.

51. The method of claim 48, wherein the distal opening in the catheter is moved in a distal to proximal direction until it is proximal to said location while drawing fluid into the distal opening.

52. The method of claim 51, further comprising moving the distal opening in the catheter in a proximal to distal direction after moving the distal opening in a distal to proximal direction.

53. The method of claim 47, wherein said catheter is delivered into the blood vessel over a guidewire.

54. The method of claim 53, wherein the guidewire includes an occlusive device at its distal end.

55. The method of claim 54, wherein the occlusive device is an inflatable balloon.

56. The method of claim 54, wherein the occlusive device is a filter.

57. A method for the evacuation of emboli from a blood vessel comprising:
   delivering a guidewire carrying an expandable device near its distal end to a location in the vessel having an occlusion on the walls of the vessel;
   actuating said expandable device to inhibit emboli in said blood vessel from migrating past said expandable device;
   positioning a catheter having a lumen in fluid communication with a distal opening in the catheter over said guidewire such that said opening is proximal to said expandable device;
   drawing fluid from the vessel into the distal opening such that emboli are carried by said fluid from said vessel into said distal opening and through said lumen of said catheter, and
   moving the distal opening of the catheter during the drawing of fluid into the distal opening in a direction such that the distal opening crosses at least a portion of the occlusion.

58. The method of claim 57, wherein the expandable device is actuated at a location distal to the occlusion.

59. The method of claim 57, wherein the distal opening of the catheter is moved during the drawing of fluid in a direction such that the distal opening crosses at least a portion of the occlusion.

60. The method of claim 57, wherein the emboli are carried through said lumen of said catheter in a distal to proximal direction.

61. The method of claim 57, further comprising, prior to drawing fluid from the vessel into the distal opening, performing therapy on said occlusion, the performing of therapy causing emboli to break off from the occlusion.

62. The method of claim 57, wherein the expandable device is an inflatable balloon.

63. The method of claim 57, wherein the expandable device is a filter.

64. The method of claim 57, wherein the distal opening of the catheter is moved in a distal to proximal direction during the drawing of fluid.

65. The method of claim 57, wherein the distal opening of the catheter is moved in a proximal to distal direction during the drawing of fluid.

66. The method of claim 65, wherein the distal opening of the catheter is moved in a proximal to distal direction after moving the distal opening of the catheter in a distal to proximal direction during the drawing of fluid.

67. The method of claim 57, wherein the distal opening of the catheter is moved over a distance of about 10 cm or more during the drawing of fluid.

68. The method of claim 57, wherein the distal opening of the catheter is moved repeatedly across the occlusion during the drawing of fluid.

* * * * *

(12) EX PARTE REEXAMINATION CERTIFICATE (9127th)
United States Patent
Muni et al.

(10) Number: US 6,454,741 C1
(45) Certificate Issued: *Jul. 10, 2012

(54) ASPIRATION METHOD

(75) Inventors: Ketan P. Muni, San Jose, CA (US); Gholam Reza Zadno-Azizi, Newark, CA (US); Celso Bagaoisan, Union City, CA (US)

(73) Assignee: Medtronic Ave Inc., Santa Rosa, CA (US)

Reexamination Request:
No. 90/009,900, Apr. 19, 2011

Reexamination Certificate for:
Patent No.: 6,454,741
Issued: Sep. 24, 2002
Appl. No.: 09/537,471
Filed: Mar. 24, 2000

( * ) Notice: This patent is subject to a terminal disclaimer.

Related U.S. Application Data

(63) Continuation of application No. 08/813,807, filed on Mar. 6, 1997, now abandoned.

(51) Int. Cl.
*A61M 29/00* (2006.01)
*A61M 31/00* (2006.01)

(52) U.S. Cl. .................................. 604/96.01; 604/509
(58) Field of Classification Search .................... 604/96
See application file for complete search history.

(56) References Cited

To view the complete listing of prior art documents cited during the proceeding for Reexamination Control Number 90/009,900, please refer to the USPTO's public Patent Application Information Retrieval (PAIR) system under the Display References tab.

*Primary Examiner* — Catherine S. Williams

(57) ABSTRACT

A method for the treatment of a stenosis or an occlusion in a blood vessel in which an occlusive device is first delivered and activated at a site distal to the occlusion to at least partially occlude the vessel. A therapy catheter is then introduced to treat the occlusion and a debris removal device is delivered to aspirate debris from the vessel. The present invention eliminates the need for a separate irrigation catheter and irrigation fluid which allows the procedure to be performed quickly and efficiently, and is especially useful in the removal of occlusion from saphenous vein graft, the coronary and carotid arteries, arteries above the aortic arch and vessels of similar size and pressure.

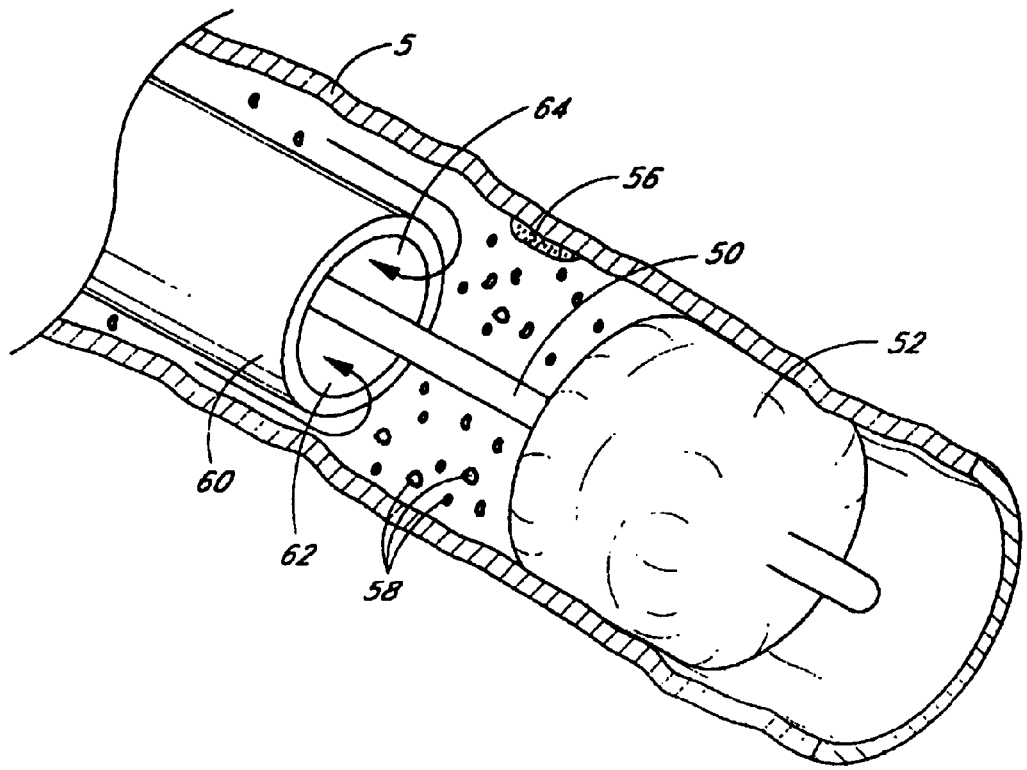

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 47-53 is confirmed.

Claims 1-46 and 54-68 were not reexamined.

* * * * *